US011382335B2

(12) United States Patent
Morrissey et al.

(10) Patent No.: US 11,382,335 B2
(45) Date of Patent: *Jul. 12, 2022

(54) METHOD OF PRODUCING LACTIC ACID

(71) Applicant: Glanbia Ireland DAC, Ballyraggat (IE)

(72) Inventors: Bill Morrissey, Thurles (IE); Colm O'Brien, Pallasgreen (IE); Magda Hogan, Kilkenny (IE); Eamon Hogan, Kilkenny (IE); Parikshit Rameshwar Sawdekar, Dublin (IE); Ramesh Babu Padamati, Lucan (IE)

(73) Assignee: GLANBIA IRELAND DAC, Ballyraggat (IE)

(*) Notice: Subject to any disclaimer, the term of this patent is extended or adjusted under 35 U.S.C. 154(b) by 0 days.

This patent is subject to a terminal disclaimer.

(21) Appl. No.: 16/324,117

(22) PCT Filed: Aug. 8, 2017

(86) PCT No.: PCT/EP2017/070120
§ 371 (c)(1),
(2) Date: Feb. 7, 2019

(87) PCT Pub. No.: WO2018/029219
PCT Pub. Date: Feb. 15, 2018

(65) Prior Publication Data
US 2019/0166865 A1 Jun. 6, 2019

(30) Foreign Application Priority Data
Aug. 8, 2016 (EP) .................................... 16183196

(51) Int. Cl.
| A23C 21/02 | (2006.01) |
| C12P 7/56 | (2006.01) |
| B01D 61/58 | (2006.01) |
| B01D 61/14 | (2006.01) |
| B01D 69/02 | (2006.01) |
| B01D 61/02 | (2006.01) |

(52) U.S. Cl.
CPC ............ *A23C 21/026* (2013.01); *B01D 61/14* (2013.01); *B01D 61/58* (2013.01); *C12P 7/56* (2013.01); *A23C 2210/206* (2013.01); *B01D 61/025* (2013.01); *B01D 61/142* (2013.01); *B01D 69/02* (2013.01); *B01D 2311/04* (2013.01); *B01D 2311/06* (2013.01); *B01D 2311/2623* (2013.01); *B01D 2311/2642* (2013.01); *B01D 2311/2673* (2013.01); *B01D 2311/2688* (2013.01)

(58) Field of Classification Search
CPC ............ A23C 21/026; A23C 2210/206; B01D 61/14; B01D 61/58; B01D 61/025; B01D 61/142; B01D 69/02; B01D 2311/04; B01D 2311/06; B01D 2311/2623; B01D 2311/2642; B01D 2311/2673; B01D 2311/2688; C12P 7/56

USPC ................................ 426/34, 41, 42, 43, 583
See application file for complete search history.

(56) References Cited

U.S. PATENT DOCUMENTS

| 4,467,034 A * | 8/1984 | Voelskow ................. C12P 7/56 435/139 |
| 5,322,781 A * | 6/1994 | Veringa ..................... C12P 7/56 435/139 |

(Continued)

FOREIGN PATENT DOCUMENTS

| EP | 0770684 A2 | 5/1997 |
| WO | 99/04903 A1 | 2/1999 |

(Continued)

OTHER PUBLICATIONS

PubChem [Internet], Bethesda (MD): National Library of Medicine (US), National Center for Biotechnology Information; 2004-. PubChem Compound Summary for CID 612, Lactic acid; [cited Aug. 12, 2020], Available from: https://pubchem.ncbi.nlm.nih.gov/compound/Lactic-acid.*

(Continued)

*Primary Examiner* — Leslie A Wong
(74) *Attorney, Agent, or Firm* — Hamilton, Brook, Smith & Reynolds, P.C.

(57) ABSTRACT

A process for producing pure lactic acid from a whey by-product rich in lactose and minerals, for example delactosed why permeate or concentrated whey permeate, is described. The method comprises upstream steps of neutralising the whey by-product with a basic metal hydroxide to form a precipitate comprising calcium and phosphate, and separating the precipitate from the whey by-product to provide a clarified whey by-product. The clarified whey by-product is fermentated by a bacterium capable of bioconversion of lactose to lactic acid to provide a fermentation broth containing a lactic acid salt. In the downstream steps, the fermentation broth is acidified to release lactic acid from the lactic acid salt, precipitate from the broth produced by acidification is removed, and the acidified fermentation broth is treated to recover pure lactic acid by removal of residual salts, and water, and optionally protein. The process of the invention produces lactic acid having a purity of 80-98% and an isomeric purity of >98% L-lactic acid using a process that employs upstream removal of divalent salts by chemical precipitation, bacterial fermentation of the demineralised substrate, and minimum downstream processing of the fermentation broth. The methods of the invention may also be employed with milk permeates.

25 Claims, 3 Drawing Sheets

(56) References Cited

U.S. PATENT DOCUMENTS

| | | | |
|---|---|---|---|
| 5,416,020 A * | 5/1995 | Severson | C12P 7/56 435/139 |
| 5,801,025 A | 9/1998 | Ohara et al. | |
| 10,927,390 B2 | 2/2021 | O'Connor et al. | |
| 2011/0306083 A1 | 12/2011 | Mucha | |
| 2018/0312885 A1 | 11/2018 | O'Connor et al. | |
| 2019/0166865 A1 | 6/2019 | Morrissey et al. | |

FOREIGN PATENT DOCUMENTS

| | | |
|---|---|---|
| WO | 01/92555 A1 | 12/2001 |
| WO | 2010103548 A2 | 9/2010 |

OTHER PUBLICATIONS

International Preliminary Report on Patentability for International Application No. PCT/EP2017/070120, "A Method of Producing Lactic Acid" dated Feb. 12, 2019.

International Search Report and the Written Opinion for International Application No. PCT/EP2017/070120, "A Method of Producing Lactic Acid" dated Nov. 22, 2017.

Payot, T, et al.; "Lactic acid production by Bacillus coagulans—Kinetic studies and optimization of culture medium for batch andcontinuous fermentations" Enzyme and Microbial Technology, 24, 191-199, 1999 (Year: 1999).

International Preliminary Report on Patentability for International Application No. PCT/IE2016/000020, "A Method for Producing Lactic Acid by Bacterial Fermentation" dated May 1, 2018.

Hu et al., "High-titer lactic acid production from NaOH-pretreated corn stover by Bacillus coagulans LA204 using fed-batch simultaneous saccharification and fermentation under non-sterile condition," Bioresource Technology, vol. 182, Feb. 11, 2015, pp. 251-257.

Juturu et al., "Production of high concentration of L-lactic acid from oil palm empty fruit bunch by thermophilic Bacillus coagulans JI12," Biotechnology and Applied Biochemistry, 2018 (published online Jul. 11, 2017), pp. 145-149.

Ou et al., "L(+)-Lactic acid production from non-food carbohydrates by thermotolerant Bacillus coagulans," J. Ind Microbiol. Biotechnol., vol. 38, 2011 (published online Aug. 9, 2010), pp. 599-605.

Ouyang et al., "Open fermentative production of L-lactic acid by Bacillus sp. strain NL01 using lignocellulosic hydrolyzates as low-cost raw material," Bioresource Technology, vol. 135, Oct. 5, 2012, pp. 475-480.

Pleissner et al., "Separation of lactic acid and recovery of salt-ions from fermentation broth," J. Chem. Technol. Biotechnol., Society of Chemical Industry, Research Article, Wiley Online Library, vol. 92, Jun. 22, 2016, pp. 504-511.

Rosenberg et al., "High temperature lactic acid production by Bacillus coagulans immobilized in LentiKats," Biotechnology Letters, vol. 27, 2005, pp. 1943-1947.

Sun et al., "Diammonium phosphate stimulates transcription of L-lactate dehydrogenase leading to increased L-lactate production in the thermotolerant Bacillus coagulans strain," Appl. Microbiol. Biotechnol., vol. 100, Feb. 17, 2016, pp. 6653-6660.

Ye et al., "Highly efficient production of L-lactic acid from xylose by newly isolated Bacillus coagulans C106," Bioresource technology, vol. 132, Jan. 16, 2013, pp. 38-44.

Zhou et al., "Efficient production of L-lactic acid by newly isolated thermophilic Bacillus coagulans WCP10-4 with high glucose tolerance," Appl. Microbiol. Biotechnol., vol. 97, Jan. 25, 2013, pp. 4309-4314.

International Search Report and Written Opinion for Int'l Application No. PCT/IE2016/000020, titled: A Method for Producing Lactic Acid By Bacterial Fermentation, dated Jan. 20, 2017.

Blascovich, "L-Latic acid production by bacteria", URL: http://www.ucd.ie/science/international_students/poster/iz_blascovich.pdf, p. 1 (2013).

Blascovich, "UCD Science Study Abroad Research Projects", University College Dublin, URL: http://www.ucd.ie/science/international_students/ (2014).

Abdel-Rahman et al., "Recent advances in lactic acid production by microbial fermentation processes", Biotechnology Advances, vol. 31, No. 6, pp. 877-902 (2013).

Michelson et al., "L(+)-Lactic acid producer Bacillus coagulans SIM-7 DSM 14043 and its comparison with *Lactobacillus delbrueckii* ssp. *lactis* DSM 20073" Enzyme and Microbial Technology, Stoneham, MA, US, vol. 39, No. 4, pp. 861-867 (2006).

Notice of Allowance for U.S. Appl. No. 15/772,046, titled: "A Method for Producing Lactic Acid by Bacterial Fermentation", dated Oct. 22, 2020.

Notice of Allowance for U.S. Appl. No. 15/772,046, titled: "A Method for Producing Lactic Acid by Bacterial Fermentation", dated Jul. 6, 2020.

Non-Final Office Action for U.S. Appl. No. 15/772,046, titled: "A Method for Producing Lactic Acid by Bacterial Fermentation", dated Jan. 2, 2020.

* cited by examiner

Procedure:

Take Whey permeate (WP) or DLP sample

⬇

Neutralize sample till pH 7 using calcium hydroxide powder

⬇

Heat the sample at 60°C for 20 min

⬇

Centrifuge the sample at 8000RPM for 7min

⬇

Discard solid pellet and collect the supernatant for analysis and fermentation

METHOD OF PRODUCING LACTIC ACID

This application is the U.S. National Stage of International Application No. PCT/EP2017/070120, filed Aug. 8, 2017, which designates the U.S., is published in English, and claims priority under 35 U.S.C. § 119 or 365(c) to EP Application No. 16183196.1, filed Aug. 8, 2016. The entire teachings of the above applications are incorporated herein by reference.

FIELD OF THE INVENTION

The present invention relates to methods of producing lactic acid. Also contemplated is pure lactic acid produced according to the method of the invention.

BACKGROUND TO THE INVENTION

Delactose whey permeate (DLP) is by-product of whey processing in dairy industry. DLP is rich in lactose (200-400 g/lit) which makes it a potential substrate for fermentation for the production of lactic acid. However, DLP also contains proteins, amino acids and a very high content of minerals such as sodium, phosphates, magnesium, calcium, potassium and chlorides along with lactose. The lactic acid producing bacteria cannot grow on whey by-products due their combined high mineral and sugar content. Also, the presence of minerals makes the recovery of lactic acid more complex and very expensive when these substrates are used for production lactic acid by fermentation.

WO01/92555 discloses a method of producing lactic acid by fermentation of a sugar containing solution such as whey permeate, ultrafiltration of the broth to provide a polymer-free permeate and acidification of the permeate to release lactic acid, and isolating lactic acid by nanofiltration or reverse osmosis.

WO99/04903 discloses a method of demineralisation of cheese whey permeate involving ultrafiltration optionally in combination with chemical precipitation.

It is an object of the invention to overcome the above-referenced problem.

SUMMARY OF THE INVENTION

The present invention is based on the finding that highly pure lactic acid can be produced by bacterial fermentation of lactose and mineral rich whey permeates from the dairy industry. In particular, the Applicant has developed a process, generally a three-stage process, for producing highly pure lactic acid from whey by-products enriched in lactose and minerals, involving upstream processing of the whey permeate (i.e. by chemical precipitation) to remove minerals and provide a clarified whey permeate, bacterial fermentation of the clarified whey permeate to provide a fermentation broth comprising a lactic acid (generally in the form of a lactic acid salt such as calcium lactate), and downstream processing of the fermentation broth to recover pure lactic acid. In one embodiment, the fermentation broth is subjected to acidification to release lactic acid from the lactic acid salt. In one embodiment, the upstream processing involves neutralisation of the whey by-product with a base, for example an alkali metal hydroxide which typically precipitates out over 50% of the calcium and phosphate salts which can be removed from the substrate by a separation process such as centrifugation. The removal of salts at the upstream processing stage has been found to significantly enhance bacterial fermentation increasing the amount of lactic acid in the fermentation broth from about 100 g/L to about 130 g/L (Table 4). In addition, it is economically advantageous as it can be achieved by means of chemical precipitation, whereas demineralisation at the downstream processing stage requires more complicated and expensive membrane or electrodialysis separation technology, which produces a liquid effluent which is costly to dispose of. This step also has the advantage of optimising the pH of the substrate for subsequent bacterial fermentation. In one embodiment, the upstream processing comprises a step of filtering the substrate to remove mono-valent ions, for example by means of nanofiltration/diafiltration. The process of the invention can also be employed with other permeates obtained from milk processing that are low in protein and rich in lactose and minerals, for example milk protein concentrate (MPC) permeates.

According to a first aspect of the present invention, there is provided a process for producing lactic acid of high purity from a milk or whey by-product rich in lactose and minerals (hereafter "whey by-product" or "milk by-product", and together "by-product"), the method comprising the steps of:

neutralising the milk or whey by-product (typically with a basic metal hydroxide) to precipitate divalent ions (typically calcium and phosphate); separating the precipitate from the milk or whey by-product to provide a clarified milk or whey by-product;

incubating the clarified milk or whey by-product with a bacterium capable of bioconversion of lactose to lactic acid to provide a fermentation broth containing a lactic acid salt; acidification of the fermentation broth to release lactic acid from the lactic acid salt; and treatment of the acidified fermentation broth to recover pure lactic acid.

The method of the invention provides a simple process for producing pure lactic acid from complex lactose and mineral rich milk or whey by-products, that is economically advantageous compared with prior art methods. First, the bulk of demineralisation is carried out upstream by means of chemical precipitation, thereby reducing the amount of demineralisation that is required downstream (post fermentation). As downstream demineralisation has to be performed with membrane separation, reducing the amount of downstream demineralisation avoids the need for extensive membrane separation and thus reduces the cost of the overall process. Secondly, the use of a basic metal hydroxide as a means of chemical precipitation neutralises the pH of the milk or whey by-product and removes minerals that inhibit microbial growth, providing an ideal environment for bacterial fermentation. Thirdly, removal of minerals upstream by chemical precipitation provides a solid by-product, which is easier and cheaper to dispose of compared with the liquid by-products generated when demineralisation is carried out at the downstream stage. This is a significant economical consideration. In addition, the whey feedstock produced by upstream chemical demineralisation has proven to be a much better feedstock compared to untreated whey by-product for bacterial fermentation, allowing significantly enhanced bioconversion of lactose to lactic acid.

In one embodiment, the basic metal hydroxide is calcium hydroxide.

In one embodiment, the whey by-product is delactosed whey permeate or concentrated whey permeate.

In one embodiment, the milk by-product is milk permeate or milk protein concentrate (MPC) permeate.

In one embodiment, the process includes a step of filtering the clarified milk or whey by-product to remove monovalent ions.

In one embodiment, the clarified milk or whey by-product is treated with nanofiltration.

In one embodiment, the clarified milk or whey by-product is treated with nanofiltration followed by diafiltration.

In one embodiment, the clarified milk or whey by-product is diluted 1:3 to 1:5 prior to nanofiltration.

In one embodiment, the nanofiltration/diafiltration employs a membrane having a molecular weight cut-off of 100-400 Daltons.

In one embodiment, the nanofiltration/diafiltration employs a membrane having a molecular weight cut-off of about 150-300 Daltons.

In one embodiment, the milk or whey by-product is heated after neutralisation and prior to separation.

In one embodiment, the milk or whey by-product is heated at 50° C. to 70° C. for 10 to 30 minutes after neutralisation. In one embodiment, the milk or whey by-product is mixed during heating to ensure homogenous heating of the whey by-product.

In one embodiment, the precipitate is removed by centrifugation. In one embodiment, the precipitate is centrifuged for 8000 RPM for 7 minutes. Other methods for removing precipitate will be apparent to a person skilled in the art, for example, microfiltration, ultrafiltration, or other suitable membrane filtration processes. The precipitate has an average dimension in the micron range.

In one embodiment, the metal hydroxide is added to the milk or whey by-product as a powder.

In one embodiment, the milk or whey by-product is neutralised by calcium hydroxide. In one embodiment, the calcium hydroxide is dry powder of calcium hydroxide. Other metal hydroxides may be employed to neutralise the substrate and precipitate our salts, for example sodium hydroxide, magnesium hydroxide, and potassium hydroxides.

In one embodiment, the upstream processing reduces the calcium levels in the milk or whey by-product by at least 50%, 60% or 70%. In one embodiment, the upstream processing reduces the calcium levels in the milk or whey by-product by at least 50% to 80%. In one embodiment, when the whey by-product is delactosed whey permeate, the upstream processing reduces the calcium levels in the whey by-product by 65 to 85%, ideally 70 to 75%. In one embodiment, when the whey by-product is whey permeate, the upstream processing reduces the calcium levels in the whey by-product by 50 to 70%, ideally 55 to 61%. % values provided are % dry weight unless otherwise indicated.

In one embodiment, the upstream processing reduces the phosphate levels in the whey by-product by at least 60%, 70% or 80%. In one embodiment, the upstream processing reduces the calcium levels in the whey by-product by at least 60% to 95%. In one embodiment, when the whey by-product is delactosed whey permeate, the upstream processing reduces the phosphate levels in the whey by-product by 75 to 95%, ideally 80 to 90%. In one embodiment, when the whey by-product is whey permeate, the upstream processing reduces the calcium levels in the whey by-product by 60 to 80%, ideally 65 to 71%.

The % reduction values provided above for calcium and phosphate are based on a mg/kg parameter. Thus, if liquid DLP contains 1000 mg calcium per Kg pre-treatment, and 300 mg per Kg post-treatment, this correlates with a 70% reduction in calcium. Examples for specific whey permeate and DLP samples are provided in Table 1.

The reduction in calcium and phosphate levels achieved according to the process of the invention have been found to be sufficient to facilitate bacterial growth in the clarified milk or whey by-product, facilitate downstream processing, while leaving a sufficient level of divalent ion nutrients in the clarified by-product for bacterial growth.

In one embodiment, the fermentation broth is treated to remove bacterial cells prior to acidification. In one embodiment, the bacterial cells are removed by centrifugation.

In one embodiment, the fermentation broth is acidified to about pH 2. In one embodiment the broth is acidified with sulphuric acid.

In one embodiment, a precipitate formed by acidification is separated from the fermentation broth. In one embodiment, the precipitate is removed by centrifugation. In one embodiment, in which acidification is achieved using sulphuric acid, the precipitate is gypsum.

In one embodiment, the acidified fermentation broth is treated with ultrafiltration to provide a lactic acid containing permeate. In one embodiment, the UF employs a membrane having a molecular weight cut-off of between 800 and 1200 Daltons. This step removes protein from the fermentation broth.

In one embodiment, the lactic acid containing permeate is treated with ion exchange to remove ions from the permeate. In one embodiment, the ion exchange is cation exchange. In one embodiment, the ion exchange is anion exchange. In one embodiment, the permeate is treated with cation exchange and anion exchange.

In one embodiment, the recovered lactic acid has a purity of at least 70%, 75%, 80%, 85%, 90%, 95%, or 98% (as determined by HPLC). In one embodiment, the recovered lactic acid has an isomeric purity of at least 95% L-lactic acid as determined by HPLC. In one embodiment, the lactic acid has an isomeric purity of at least 99% L-lactic acid as determined by HPLC.

In one embodiment, the acidified fermentation broth is filtered to remove colour from the broth. In one embodiment, the filter is charcoal.

In one embodiment, the deionised permeate is de-watered. In one embodiment, the deionised fermentation broth is de-watered by evaporation.

In one embodiment, the bacterium capable of converting lactose into lactic acid is selected from a *Lactobacillus* or a *Bacillus* strain.

In one embodiment, the *Bacillus* bacterium is a *Bacillus coagulans*.

Examples of bacteria capable of bioconversion of lactose in substrates into lactic acid are described in the literature, for example Abdel-Rahman et al (Biotechnology Advances, Vol. 31, No. 6, November 2013), Michelson et al (Enzyme and Microbial Technology, Vol. 39, No: 4, August 2006), and WO2010/103548 which discloses *Bacillus coagulans* MTCC 5454 deposited at the Microbial Type Culture Collection and Gene Bank (MTCC), Institute of Microbial Technology (IMTECH), Sector 39A, Chandigarh, India. Other methods of producing bacteria capable of bioconversion of lactose in substrates into lactic acid are described in Examples 3 and 4 below.

In one embodiment, the bacterium is capable of growing on a test culture medium containing at least 10% delactosed whey permeate (v/v) and converting DLP into lactic acid at a yield of at least 50%.

In one embodiment, the fermentation step comprises batch fermentation of the clarified whey permeate.

In one embodiment, the batch fermentation is fed batch fermentation.

In one embodiment, the clarified milk or whey permeate is the predominant energy source of the bacteria (i.e. at least 80-% of the energy source by weight) during fermentation.

In one embodiment, the clarified milk or whey permeate is the sole energy source for the bacteria during fermentation.

In another aspect, the invention provides a pure lactic acid obtained by the method of the invention. In one embodiment, the lactic acid has a purity of at least 70%. In one embodiment, the lactic acid has a purity of at least 80%. In one embodiment, the lactic acid has an isometric purity of at least 95% L-lactic acid. In one embodiment, the lactic acid has an isometric purity of at least 98% L-lactic acid.

Other aspects and preferred embodiments of the invention are defined and described in the other claims set out below.

DETAILED DESCRIPTION OF THE INVENTION

Figure 1:
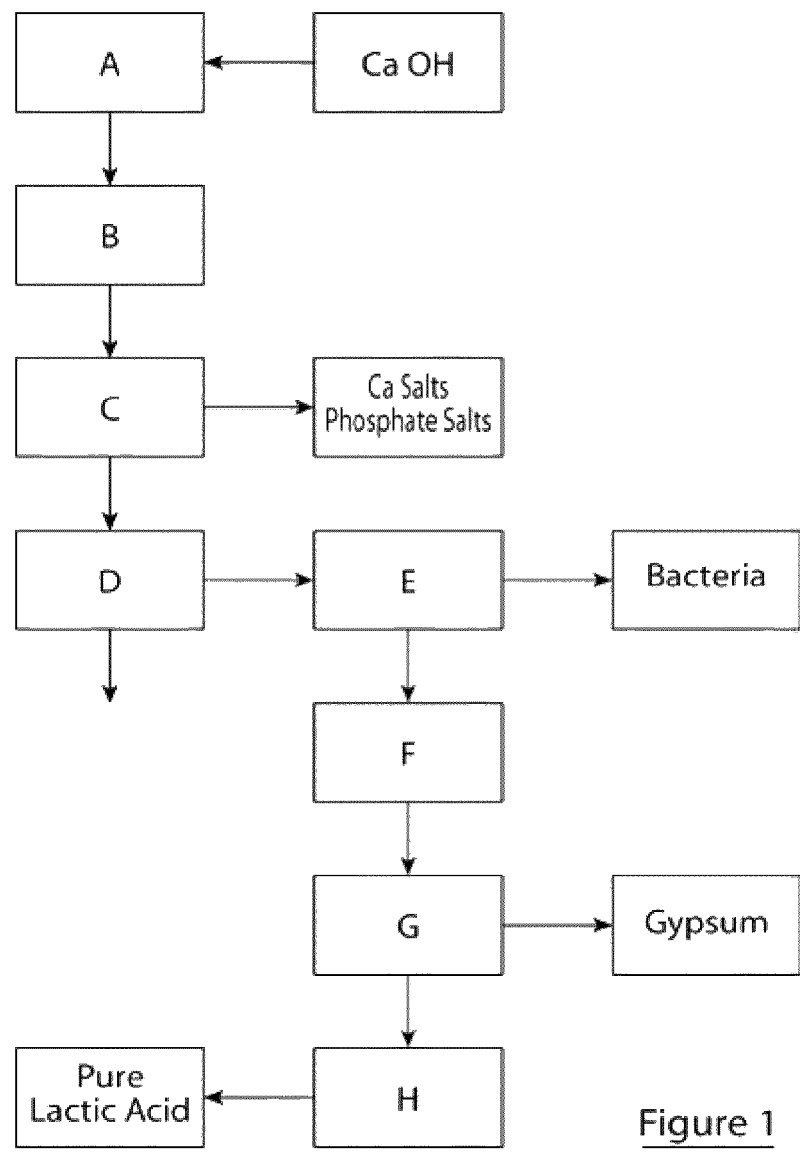
FIG. 1 is an illustration of the method of the invention showing the initial upstream processing step to provide a clarified whey by-product depleted in divalent ions, bacterial fermentation of the clarified whey product to provide a fermentation broth comprising calcium lactate, and downstream processing of the fermentation broth to release lactic acid and concentrate the lactic acid.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

"Lactic acid" is an organic compound with the formula $CH_3CHCO_2H$. It is a chiral compound existing in two forms, known as optical isomers, namely D-lactic and L-lactic acid. In the current embodiment, the lactic acid produced with the process and adapted bacteria of the invention is predominantly L-lactic acid (for example >98% w/w).

"Whey by-product rich in lactose and minerals" or "whey by-product" means a liquid by-product of whey processing that contains at least 30 g/L lactose and having a high mineral content (for example at least 1000 ppm chloride). In one embodiment, the whey by-product has at least 1100, 1200, 1300, 1400 or 1500 ppm chloride. Generally, the whey by-product is produced when liquid whey is fractionated to remove protein leaving a permeate rich in lactose and minerals. The term includes whey permeate, concentrated whey permeate, and delactosed whey permeate. In one embodiment, the whey by-product contains at least 40 g/L, 50 g/L, 60 g/L, 70 g/L, 80 g/L, 90 g/L, 100 g/L, 120 g/L, 140 g/L, 160 g/L, 180 g/L, 200 g/L, 210 g/L, 220 g/L, 230 g/L or 240 g/L lactose. Lactose, glucose, galactose and lactic acid concentrations were determined on a high-performance liquid chromatography (HPLC, Agilent series 1200, Japan) system equipped with a refractive-index detector. The HPLC column used was Aminex 87H (Bio-Rad, Hercules, Calif.) with 5 mM sulphuric acid as the mobile phase at a flow rate of 0.6 mL/min whiles the column temperature was maintained at 50° C.

"Milk by-product rich in lactose and minerals" or "milk by-product" means a liquid by-product of milk processing that contains at least 30 g/L lactose and having a high mineral content (for example at least 5000 ppm ash). Generally, the milk by-product is produced when milk is fractionated to remove protein leaving a permeate rich in lactose and minerals. The term includes milk protein concentrate permeate. Lactose, glucose, galactose and lactic acid concentrations were determined on a high performance liquid chromatography (HPLC, Agilent series 1200, Japan) system equipped with a refractive-index detector. The HPLC column used was Aminex 87H (Bio-Rad, Hercules, Calif.) with 5 mM sulphuric acid as the mobile phase at a flow rate of 0.6 mL/min whiles the column temperature was maintained at 50° C.

"Whey permeate": Whey is the liquid remaining after milk has been curdled and strained. It is a by-product of the manufacture of cheese and casein. It can exist as sweet whey or acid whey. The whey may be obtained from bovine milk or milk from other mammals such as goats or sheep. Preferably, the milk is bovine milk. Whey permeate is produced by removing protein and other solid components from whey. It is generally produced by treating liquid whey to ultrafiltration or diafiltration. Whey permeate typically contains at least 40 g lactose per litre. Typically, whey permeate contains 1900 to 10,000 or more ppm chloride. An exemplary composition of whey permeate is provided in Table 7 below.

"Concentrated whey permeate" (CWP) refers to a product derived from whey permeate evaporation. Typically, concentrated whey permeate contains 200-240 g lactose per litre. An exemplary composition of CWP is provided in Table 8 below.

"Delactosed whey permeate" is a by-product of processing of whey permeate to remove lactose. However, it has a higher amount of lactose post-filtration compared with whey permeate, and higher amounts of salts and minerals, especially chlorides and phosphates. Typically DLP contains at least 240 g lactose per litre. Typically, DLP contains 15,000 to 62,000 ppm chloride. An exemplary composition of delactosed whey permeate is provided in Table 6 below.

"Neutralising" as applied to the milk or whey by-product means adding a base to the milk or whey by-product to bring the pH at or close to neutral, at which pH divalent calcium and phosphate ions in the milk or whey precipitate and can be removed from the substrate. In a preferred embodiment, the base is a basic metal hydroxide. Exemplary metal hydroxides include sodium hydroxide and calcium hydroxide. Table 1 below shows that alkali metal hydroxide precipitation can reduce the calcium content of whey permeate from 1957 mg/Kg to 621 mg/Kg, and delactosed whey permeate from 5783 mg/Kg to 1597 mg/Kg, reduction of over 60%. Likewise, the phosphate content of whey permeate can be reduced from 3396 mg/Kg to 1074 mg/Kg, and delactosed whey permeate from 3954 mg/Kg to 515 mg/Kg, reduction of over 60% and 85%, respectively. Table 5 illustrates that different basic metal hydroxides, can be employed to remove calcium and phosphate from the whey product.

"Metal hydroxide" refers to metal hydroxides that are basic such as sodium hydroxide and calcium hydroxide. The term includes alkali metal hydroxides and Alkaline earth metal hydroxides. Specific hydroxides include sodium hydroxide, calcium hydroxide, barium hydroxide, magnesium hydroxide, and potassium hydroxide. Typically, the metal hydroxide is employed in a dry powder form or in solution. Typically, a sufficient amount of metal hydroxide is added to the milk or whey by-product to neutralise the milk or whey by-product.

"Nanofiltration/Diafiltration" refers to a process of nanofiltration in which the feed is diluted prior to nanofiltration. In one embodiment, the feed is diluted 1:2, 1:3, 1:4, 1:5 or 1:6 times. In one embodiment, nanofiltration employs a membrane having a molecular weight cut-off of 100-400 Daltons, preferably 150-300 Daltons. In one embodiment, the nanofiltration.diafiltration step employs a GE Osmonic Membrane with a 150-300 Dalton cut-off.

"Acidification" refers to a process in which acid is added to fermentation broth to reduce the pH sufficiently to release lactic acid from the lactic acid salt (i.e. calcium lactate), for example a pH of 1 to 3. In one embodiment, the acid is sulphuric acid, in which a gypsum precipitate is produced. Other acids may be employed for acidification, for example hydrochloric acid, nitric acid, phosphoric acid.

"Treatment of the acidified fermentation broth to recover pure lactic acid" refers to a step or series of steps to remove components from the fermentation broth as part of the process of recovery and purification of lactic acid. In one embodiment, the components include one or more of protein, chromophores, and salts. In one embodiment, the downstream treatment (upstream treatment includes one or more of ultrafiltration, cation exchange, anion exchange, charcoal filtration, and evaporation). In one embodiment, the process comprises ion exchange and evaporation. In one embodiment, the process comprises cation exchange and anion exchange and evaporation. In one embodiment, the process comprises cation exchange, anion exchange, charcoal filtration and evaporation. In one embodiment, the process comprises ultrafiltration, cation exchange, anion exchange, charcoal filtration and evaporation.

"Ultrafiltration" refers to a membrane separation process that in one embodiment employs a membrane having a molecular weight cut-off of about 1 kDa (for example 750 Dalton to 1250 Dalton). Ultrafiltration may be employed either upstream or downstream of the microbial fermentation step. For example, it may be employed to remove precipitate during clarification of the substrate, or it may be employed to remove protein from the fermentation broth after microbial fermentation.

"Ion exchange" refers to a process of exchange of ions between two electrolyte solutions, one of which is the fermentation broth (or the permeate of the fermentation broth). Ion exchange may be anion exchange or cation exchange, or both. The purpose of ion exchange when it is employed it to reduce the mineral level of the fermentation broth, and thereby purify the lactic acid. Many minerals are often added to the fermentation broth during fermentation (i.e. as part of the culture broth), and these minerals generally need to be removed as part of the treatment of the fermentation broth and recovery of lactic acid. In one embodiment, the ion exchange process comprises cation exchange and anion exchange processes. Resin made from macroporous polystyrene crosslinked with divinylbenzene having functional group sulphonic acid or carboxylic acid was used in the process for cations removal, similarly macroporous polyacrylic crosslinked with divinylbenzene having functional group of Tertiary Amine or Quaternary Ammonium ions was selected for demineralisation. Cation exchange resins C180S obtained from Purolite LTD, TPS 1013 obtained from Jacobi LTD and Dowex Marathon C-10 (H) from Dow LTD were used for cations removal. In Anion exchange resin, A845s supplied by Purolite LTD, TPS 1019 obtained from Jacobi LTD, Dowex Marathon WBA-2 and Dowex Marathon OH-form from Dow LTD were used for anions removal. All resins were packed in jacketed glass column and fermentation feed solution were passed into the column at different flow rate (0.2-0.02× Bed Volume) to achieve complete demineralisation. All resins operation was operated in FBR (fluidised bed reactor) system at 40-60° C. Cation and anion exchange resins suitable for use in the present invention are described more fully in Zagorodni et al (Ion Exchange Materials: Properties and Applications, Elsevier, Amsterdam, 2006 ISBN: 0-08-044552-7).

"Pure lactic acid" or "lactic acid of high purity" or "highly pure lactic acid" refers to lactic acid having a purity of at least 70% as determined by HPLC. In one embodiment, the process of the invention produces lactic acid having a purity of at least 80%, 85%, 90%, 95% or 98%.

"Bacteria capable of converting lactose into lactic acid" is generally selected from a *Lactobacillus* or a *Bacillus* strain, especially a strain of *Bacillus coagulans*. Examples of bacteria capable of bioconversion of lactose in substrates into lactic acid are described in the literature, for example Abdel-Rahman et al (Biotechnology Advances, Vol. 31, No. 6, November 2013), Michelson et al (Enzyme and Microbial Technology, Vol. 39, No: 4, August 2006), and WO2010/103548 which discloses *Bacillus coagulans* MTCC 5454 deposited at the Microbial Type Culture Collection and Gene Bank (MTCC), Institute of Microbial Technology (IM-TECH), Sector 39A, Chandigarh, India. Other methods of producing bacteria capable of bioconversion of lactose in substrates into lactic acid are described in Examples 3 and 4 below.

"*Bacillus coagulans*" is a lactic acid forming bacterial species within the genus *Bacillus*. It is a gram-positive rod, and generally catalase forming, spore forming, motile and a facultative anaerobe. An example of a *Bacillus coagulans* is a strain of *Bacillus coagulans* MG-2 isolated from soil and identified by 16S rDNA sequencing (See Example 5). Other examples of *Bacillus coagulans* are described in the literature and available from Depository Institutions such as the NCIMB in Scotland (http://www.ncimb.com/) and DSMZ in Germany (https://www.dsmz.de/). In one embodiment, the *Bacillus coagulans* is an adapted *Bacillus* strain.

"Adapted *Bacillus* strain" means a strain of *Bacillus*, typically a strain of *Bacillus* coagulans, that has been adapted in an adaption process to be more tolerant to whey by-product such as whey permeate or DLP than the non-adapted (starting) strain. In one embodiment, the adapted *Bacillus* strain has been adapted according to a method of Example 4. Examples of adapted strains are described in Example 4 (UCD1 and UCD2). The starting *Bacillus* strain can be isolated from nature or obtained from a culture deposit. An example of a starting strain is MG-2 strain described below.

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Referring to FIG. 1, there is illustrated a general process of the invention for producing pure lactic from a whey by-product using bacterial fermentation. In a first step A, the whey by-product is neutralised using a basic alkali metal, bringing the PH of the whey by-product to about 7. In a second step, B, the neutralised whey by-product is optionally heated to facilitate precipitation of calcium and phosphate salts, which are removed from the whey by-product in a separation step C. In step D, the clarified whey by-product is added to a reactor along with an inoculum of a bacteria capable of bioconversion of lactose into lactic acid, and a suitable culture medium, and incubated for a period of time, generally between 20 and 50 hours at 40-50° C., that is sufficient to allow the bacteria metabolise the lactose in the fermentation broth producing lactic acid which is typically converted into a lactic acid salt (generally calcium lactate). In step E, the fermentation broth is optionally treated (i.e. by centrifugation) to remove the bacteria. In step F, the broth is acidified with a suitable acid to release lactic acid from the calcium lactate, producing a further calcium precipitate. When the acid used for acidification is sulphuric acid, the calcium precipitate is gypsum (calcium sulphate). In step G, a further centrifugation step removes the gypsum precipitate from the broth. In step H, the fermentation broth is treated to recover and purify the lactic acid, using one or more separation steps (for example ultrafiltration to remove protein, and cation and anion exchange to remove residual minerals in the broth) and optionally dewatering to concentrate the lactic acid.

Example 1

Figures 2, 3:
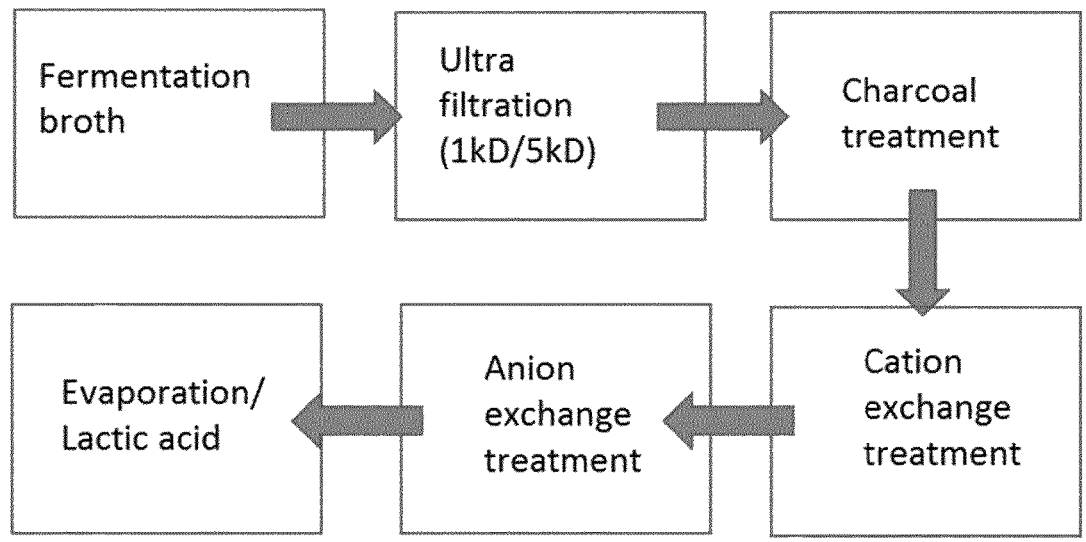
FIG. 2 is an illustration of one embodiment of the upstream processing of the whey by-product, in this case delactosed whey permeate.
FIG. 3 is an illustration of a first embodiment of the downstream processing steps forming part of the process of the invention.
Figure 4:
FIG. 4 shows the visual appearance of the fermentation broth after each of the downstream processing steps of FIG. 3.

Referring to FIGS. 2 to 4, there is illustrated an embodiment of the process of the invention for producing lactic acid from a whey by-product and comprising upstream processing steps (FIG. 2), a bacterial fermentation step, and downstream processing steps (FIG. 3).

A: Upstream Processing

Referring to FIG. 2, the upstream processing steps are illustrated. The substrate, in this case either delactosed whey permeate (DLP) or whey permeate (WP), is neutralised with calcium hydroxide powder (30% wt/vol) to bring the PH of the substrate to about 7. The sample is then heated at 60° C. for 20 minutes to assist with precipitation of calcium and phosphate, and the substrate is then centrifuged at 8000 RPM for 7 minutes to remove the precipitate. The supernatant is retained for analysis and further processing. An analysis for the supernatant is provided in Table 1.

TABLE 1

Average composition of whey permeate and DLP before and after calcium hydroxide treatment

| | Whey permeate (WP) | After Ca(OH)$_2$ treatment | DLP | After Ca(OH)$_2$ treatment |
|---|---|---|---|---|
| pH | 4.92 | 6.96 | 3.67 | 6.92 |
| Total solid (% w/w) | 23.9 | 15.38 | 35.94 | 23.9 |
| Ash (% w/w) | 4.73 | 4.21 | 3.3 | 2.2 |
| Calcium (mg per kg) | 1957 | 621 | 5783 | 1597 |
| Magnesium (mg per kg) | 568 | 268 | 837 | 500 |
| Total phosphate (mg per kg) | 3396 | 1074 | 3954 | 515 |
| Potassium (mg per kg) | 12497 | 13053 | 5725 | 5784 |
| Sodium (mg per kg) | 7189 | 7663 | 2444 | 2628 |
| Chloride (%) | 1.4 | 1.53 | 1.18 | 1.43 |
| Lactose (% w/w) | 20.02 | 21.85 | 33.12 | 29.87 |

The use of calcium hydroxide precipitation resulted in 58% and 78% reduction in calcium from whey permeate and delactosed whey permeate, respectively, and 68% and 86% reduction in total phosphate from whey permeate and delactosed whey permeate, respectively. In addition, magnesium is reduced by 30 to 50%.

In a next step, the supernatant is treated to remove monovalent ions. This step facilitates subsequent bacterial fermentation and downstream processing of the fermentation broth, and involves treating the clarified whey by-product to nanofiltration/diafiltration using a GE-Osmonic membrane with 150-300 Dalton cut-off and 4× or 5× volumes of diafiltration water. An analysis of the nanofiltered DLP is provided in Table 2.

TABLE 2

Nano filtration of pre-treated DLP sample

| NF Diafiltration | ASH % | TS % | % ASH: (TS %) | Sodium (ppm) | Potassium (ppm) | Magnesium (ppm) | Chloride (ppm) | Calcium (ppm) | Phosphate (ppm) |
|---|---|---|---|---|---|---|---|---|---|
| NF feed CDLP | 5.02 | 21.20 | 23.67 | 9056 | 16426 | 177 | 20800 | 50 | 1250 |
| 1:4 dilution | 2.16 | 16.27 | 13.27 | 3153 | 5152 | 129 | 5690 | 81 | 969 |

TABLE 2-continued

Nano filtration of pre-treated DLP sample

| NF Diafiltration | ASH % | TS % | % ASH: (TS %) | Sodium (ppm) | Potassium (ppm) | Magnesium (ppm) | Chloride (ppm) | Calcium (ppm) | Phosphate (ppm) |
|---|---|---|---|---|---|---|---|---|---|
| 1:5 dilution | 1.67 | 14.21 | 11.75 | 2196 | 3419 | 118 | 3490 | 86 | 956 |

The use of the nanofiltration/diafiltration step with 4×volumes of diafiltration water reduces the chloride concentration by 84% as a % total solids and removes ash by 50% on % total solids basis. Sodium and potassium ions were removed significantly along with chloride ions as indicated above.

B: Bacterial Fermentation

The clarified DLP substrate obtained after nanofiltration/diafiltration was employed for bacterial fermentation in a fermentation reactor.

B1: Solid Media Preparation for Strain Maintenance

The following solid components were mixed in water until completely dissolved and subsequently autoclaved at 121° C. for 15 min. (the amounts of solid additions were calculated to give the amounts below after the addition of cWP to the media)

| Yeast extract | 10 g/l |
| Bis-tris | 10 g/l |
| Agar | 15 g/l |
| NH4H2PO4 | 2 g/l |
| (NH4)2SO4 | 3.5 g/l |
| Trace element solution | 2 ml/l |
| MgSO4•7H2O | 0.04 g/l |

The nfcWP is autoclaved at 105° C. for 15 min to minimize the amount of lactose loss due to heat and pH dependent Maillard reaction. It is then mixed with the other sterile media components at the desired concentration.

| nfcWP | 10% (v/v) |

The media is adjusted to pH 6.5 with 6 M NaOH and poured into petri dishes and then allowed to solidify.

B2: Liquid Media Preparation for Primary Inoculum

The following solid components were mixed in 850 ml water until completely dissolved (the amounts of solid additions were calculated to give the amounts stated below after the addition of nfcWP to the media)

| Yeast extract | 10 g/l |
| Bis-tris | 10 g/l |
| NH4H2PO4 | 2 g/l |
| (NH4)2SO4 | 3.5 g/l |
| Trace element solution | 2 ml/l |
| MgSO4•7H2O | 0.04 g/l |

To this 150 ml of nfcWP is added, and mixed thoroughly. The media is adjusted to pH 6.5 with 6 M NaOH.
This is then passed through a 0.2 μm bottle top vacuum filtration assembly.
A final volume of 1000 ml is required to inoculate the secondary inoculum fermentation vessel.

B3: Liquid Media Preparation for Secondary Inoculum fermentation

The following solid components were mixed in 7800 ml water until completely dissolved (the amounts of solid additions were calculated to give the amounts stated below after the addition of nfcWP to the media)

| Yeast extract | 10 g/l |
| NH4H2PO4 | 2 g/l |
| (NH4)2SO4 | 3.5 g/l |
| Trace element solution | 2 ml/l |
| MgSO4•7H2O | 0.04 g/l |

To this 1200 ml of nfcWP is added, and mixed thoroughly.
The media is adjusted to pH 6.5 with 6 M NaOH.
This is then pumped through a 0.2 μm filter capsule into an empty sterilised fermentation vessel.
The pH in the fermentation vessel is maintained at pH 6.5 throughout by automatic addition of Ca(OH)2
Agitation in the vessel is controlled at 100 rpm
Temperature in the vessel is controlled at 48° C.
A final volume of 8000 ml is required to inoculate the production fermentation vessel.

B4: Fermentation Media Preparation for a Batch Process at a Final Volume of 105 l.

The following solid components were mixed in 72 l of nfcWP until completely dissolved. (the amounts of solid additions were calculated based on the final volume of the fermentation (105 l))

| Yeast extract | 6.5 g/l |
| (NH4)2HPO4 | 0.3 g/l |

The media is adjusted to pH 6.5 with 30% (w/v) Ca(OH)2 suspension and controlled at this pH for the duration of the fermentation B5: Fermentation Process and Timeline 1. The *Bacillus coagulans* UCD 2 strain should be revived from stocks at least 24 h prior to the preparation of the first inoculum.
A single loop from a slope or freezer stock should be streaked onto a solid media plate and incubated at 54° C. for 24 h.

2. A single colony of UCD 2 from this plate should then be aseptically transferred to the 1 l primary inoculum. This should be left for between 16 and 18 h in a non-shaking incubator at 54° C. and reach a minimum optical density of 0.5 when measured using a spectrophotometer set at 600 nm.

3. All of this 1 l primary inoculum should be aseptically transferred to the secondary inoculum fermenter with a final volume of 8 l. This should be incubated with agitation set at 100 rpm and temperature set to 48° C. This incubation should last 8-10 h until the OD has reached between 0.5 and 0.8. pH should be controlled for this fermentation with NaOH to allow for OD measurements.

4. All of this 8 l secondary inoculum should be transferred aseptically to the production fermenter, to give a starting volume of 80 l. This should be incubated with agitation set at 100 rpm and temperature set to 48° C. pH should be controlled for this fermentation with 30% w/v Ca(OH)2 for the production of calcium lactate.

5. The onset of rapid base addition should occur at between 3 and 6 h.

6. As mentioned the lactose concentration of the cWP is variable due to the nature of its origin and should therefore be assayed each time to determine the volumes required at each stage. This protocol assumes a 217 g/l lactose concentration in the nfcWP. Therefore the starting lactose concentration in the production fermentation should be approximately 195 g/l.

TABLE 3

Fermentation Process and Timeline

| Day 1 | Day 2 | Day 3 | Day 4 | Day 5 |
|---|---|---|---|---|
| Freezer Stock to plate | Plate to first Inoculum | First to second inoculum | Production fermentation inoculation | Harvest |

TABLE 4

Comparison of fermentations with treated and untreated WP and DLP as substrates

| Strain | Residue type | Fermentation Time (hours) | Starting Lactose (g/l) | Lactic acid (g/l) | Volumetric productivity (g/l/h) | Calcium hydroxide dilution effect | % Yield |
|---|---|---|---|---|---|---|---|
| aBC | Untreated WP | 36 | 140 | 102 | 2.8 | 1.17 | 85.2 |
| aBC | Treated WP | 20 | 190 | 131 | 6.6 | 1.23 | 84.5 |
| aBC | Untreated DLP | 60 | 140 | 101 | 1.7 | 1.18 | 85.1 |
| aBC | Treated DLP | 30 | 190 | 129 | 4.3 | 1.25 | 85.0 | aBC = adapted strain of *Bacillus coagulans*

C: Downstream Processing

DLP sample treated by the chemical precipitation process and NF/Diafiltration was effectively utilized for the lactic acid production and obtained around 100 g/L to 130 g/L of Lactic acid concentration in fermented broth sample. This broth is very complex in nature due to presence of ash and other ingredients from fermentation process such as residual carbohydrates, proteins, small peptides and minerals, which makes the downstream process more difficult. The fermentation broth contains lactic acid in the form of calcium lactate with bacterial cells. In first step of the downstream processing, bacterial cells was removed through simple centrifugation at 55° C. followed by acidification using sulphuric acid (pH-2) to release the free lactic acid in to the solution. The formed by-product gypsum was removed by centrifugation process. FIG. 3 shows the various steps developed to recover lactic acid from fermentation broth. The developed process scheme contains removal of proteins through 1 KDa UF operation, charcoal for colour, followed by demineralization using cation and then anion exchange resins. In more detail, the fermentation broth obtained after acidification and centrifugation was processed (about 3.5 L) through UF 1 KDa membrane to separate proteins; the permeate obtained after UF treatment was treated for colour removal using commercial screened charcoal packed in vertical column of dimension 50 mm ID×300 mm height and working bed volume of 500 mL packed with charcoal. The broth solutions of volume 2.4 L were passed through against gravity through the charcoal column. After charcoal treatment the fermented broth solution (1.8 L) was passed through both optimized selective cationic and anionic resins to remove the mineral ions present in the broth solution with the same column conditions. Final broth of volume 1.5 L containing 5 g/L of lactic acid concentration was concentrated up to 80% by means of evaporation. The recovered lactic acid was 80% pure with isomeric purity of 99% L-lactic acid confirmed by HPLC analysis. FIG. 4 shows the visual appearance of the fermented broth solutions after each purification step.

Example 2

The upstream processing steps described in Example 1 are repeated using a number of basic metal hydroxides (30% (wt/vol), including calcium, barium, magnesium and potassium hydroxides. The samples were characterised by ICP-MS before and after pre-treatment process to assess the level of demineralisation using the pre-treatment process. Table 5 shows the comparative elemental analysis of DLP treated with barium hydroxide, calcium hydroxide, magnesium hydroxide, potassium hydroxide and ammonia pre-treatment process. The processing steps are the same as for Example 1, with the exception that the sample was centrifuged for 4000 g×5 minutes.

TABLE 5

DLP pre-treatment using alkali metal hydroxide

| | TS % | Calcium PPM | Magnesium PPM | Sodium PPM | Potassium PPM | Phosphate PPM | Sulphate PPM | Chloride PPM |
|---|---|---|---|---|---|---|---|---|
| Raw diluted DLP | 12.5 | 1392 | 316 | 4676 | 7127 | 1663 | 611 | 9000 |
| Calcium pre-treatment | 11 | 539 | 115 | 4680 | 7120 | 270 | 613 | 9200 |

TABLE 5-continued

DLP pre-treatment using alkali metal hydroxide

| | TS % | Calcium PPM | Magnesium PPM | Sodium PPM | Potassium PPM | Phosphate PPM | Sulphate PPM | Chloride PPM |
|---|---|---|---|---|---|---|---|---|
| Barium hydroxide pre-treatment | 11 | 131 | 60 | 4503 | 6874 | 261 | <20 | 8700 |
| Mg(OH)$_2$ pre-treatment | 12 | 15 | 1079 | 4889 | 7352 | 476 | 609 | 9500 |
| KOH pre-treatment | 12 | 202 | 178 | 4766 | 11668 | 1225 | 569 | 9500 |

Example 3

Figure 5:
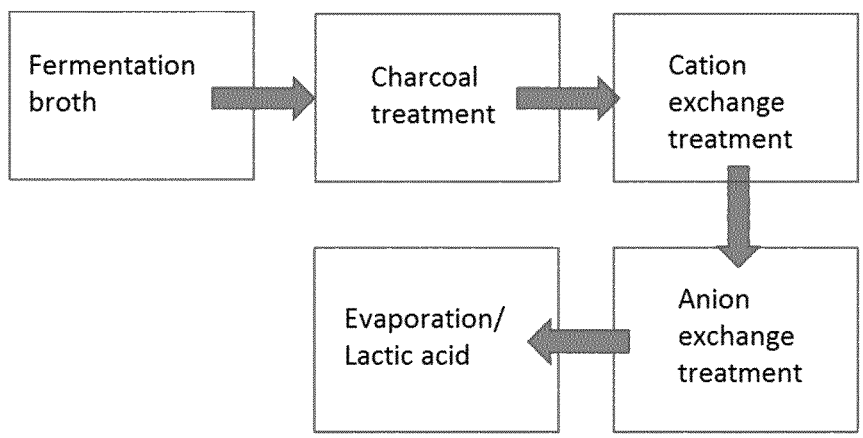
FIG. 5 is an illustration of a first embodiment of the downstream processing steps forming part of the process of the invention.
Figure 6:
FIG. 6 shows the visual appearance of the fermentation broth after each of the downstream processing steps of FIG. 5.

In this example, described with reference to FIGS. 5 and 6, the upstream processing steps, bacterial fermentation step, and initial downstream processing is the same as described in Example 1. In Example 3, fermentation broth containing 112 g/L of lactic acid was processed for downstream processing. In the first step 4.12 L of fermented was passed through charcoal column to remove colour particles. 4 L of Sample obtained after charcoal treatment was subjected for demineralization using cation exchange and anion exchange resins in packed bed column with dimensions of 50 mm ID×300 mm height. 3.5 L of colour less solution with 5 g/L lactic acid was collected after passing through anion exchange resin was concentred to 80% by evaporation. HPLC analysis indicated that recovered lactic acid is 98% pure with isomeric purity>99% of L-lactic acid. Samples obtained after each process steps were showed in FIG. 6.

Example 4

Adaptation of *Bacillus coagulans*

*B. coagulans* cannot grow on whey permeate 20% or DLP above 10% volume per volume of growth medium (v/v).

1. The WT *Bacillus coagulans* was inoculated on to solid media plates with a range of DLP concentrations (5, 10, 15, 20, 25, 30 and 35% v/v) to determine the growth threshold of the starting strain (wild type (WT)) on DLP.

2. Plates were incubated at 54° C. for 16 h, positive growth was determined as colonies matching the time taken to appear on the solid growth media as that of the WT strain when grown on TSA plates containing 5% DLP under the same incubation conditions.

3. Colonies were determined to be tolerant of 10% (v/v) DLP. Some small colonies were observed at 15% but they did not match the criteria for positive growth outlined in point 2. No colonies were observed at concentrations of 20% and above DLP.

4. Colonies from plates containing 10% DLP were transferred to liquid media containing 15% DLP, these cultures were incubated without shaking in test tubes at 54° C. for 96 hours.

5. Samples were taken from these cultures every 24 h and plated on to solid media containing 15% DLP and incubated as described in point 2. Many colonies were observed from time point 48 to 96 h, but only colonies that met the criteria for positive growth outlined in point two were taken forward for further adaptation by repeating the procedure with the colonies capable of growth at 15% DLP used as the inoculum for liquid culture with 20% DLP.

6. This process was repeated using 20 to 40% DLP over a number of months. At this point the 5% incremental increases that had been successful in adapting the strain from 10% DLP to 40% DLP tolerance ceased to deliver the same rate of adaptation. The colonies matching the criteria for positive growth at 40% were stocked and designated as *Bacillus coagulans* UCD 1

7. To adapt the strain to higher concentrations of DLP 2% increments were employed with the same sampling and screening methods as described above. These were repeated until colonies matching the criteria for positive growth were isolated on plates containing 50% DLP on solid media. These colonies were stocked and designated *Bacillus coagulans* UCD2.

8. Both UCD 1 and UCD 2 were screened for the ability to produce LA from WP and DLP, these adapted strains were capable of LA production using WP (50% v/v) and DLP (50% (v/v)) as the sole source of lactose. The Wild type strain did not grow on WP or DLP at 50% (v/v).

Example 5

Soil samples from UCD were incubated in a liquid medium containing 30% (v/v) DLP. The liquid medium was incubated for 3 weeks. Each week samples were withdrawn and plated out on solid growth media with 30% DLP (v/v). Isolates were screened for LA production. MG-2 was identified as a *Bacillus coagulans*. It produced LA when grown on WP and DLP up to 50% (v/v).

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

TABLE 6

Typical Composition of a DLP

|  | Calcium (ppm) | Phosphate (ppm) | Chloride (ppm) | Sodium (ppm) | Potassium (ppm) | Magnesium (ppm) | Sulphate (ppm) | Dry Matter (DM) % | Ash % of DM | Protein % DM | Fat % (DM) | Lactose and other organics % (DM) |
|---|---|---|---|---|---|---|---|---|---|---|---|---|
| Min | 827.5 | 4075 | 15450 | 6447.5 | 14580 | 735 | 3405 | 24 | 20 | 5 | 0.1 | 60 |
| Average | 1655 | 8150 | 30900 | 12895 | 29160 | 1470 | 6810 | 33 | 24 | 8 | 0.7 | 68 |
| Max | 3310 | 16300 | 61800 | 25790 | 58320 | 2940 | 13620 | 40 | 28 | 10 | 2 | 75 |

DM = dry matter,
PPM = part per million,
% w/w

TABLE 7

Typical composition of a Whey permeate (WP)

|  | Calcium (ppm) | Phosphate (ppm) | Chloride (ppm) | Sodium (ppm) | Potassium (ppm) | Magnesium (ppm) | Sulphate (ppm) | Dry Matter (DM) % | Ash % of DM | Protein % DM | Fat % (DM) | Lactose and other organics % (DM) |
|---|---|---|---|---|---|---|---|---|---|---|---|---|
| Min | 175 | 480 | 1900 | 569 | 1348 | 65 | 668 | 6 | 10 | 2 | 0.1 | 80 |
| Average | 349 | 960 | 3800 | 1137 | 2696 | 129 | 1337 | 10 | 14 | 4 | 0.4 | 86 |
| Max | 699 | 1920 | 7600 | 2274 | 5392 | 259 | 2673 | 12 | 18 | 6 | 1 | 90 |

DM = dry matter,
PPM = part per million,
% w/w

TABLE 8

Typical composition of a concentrated WP (CWP)

|  | Calcium (ppm) | Phosphate (ppm) | Chloride (ppm) | Sodium (ppm) | Potassium (ppm) | Magnesium (ppm) | Sulphate (ppm) | Dry Matter (DM) % | Ash % of DM | Protein % DM | Fat % (DM) | Lactose and other organics % (DM) |
|---|---|---|---|---|---|---|---|---|---|---|---|---|
| Min | 524 | 1440 | 5700 | 1705.5 | 4044 | 194 | 2005 | 18 | 7 | 2 | 0.1 | 80 |
| Average | 1048 | 2880 | 11400 | 3411 | 8088 | 388 | 4010 | 30 | 11 | 4 | 0.4 | 85.6 |
| Max | 2096 | 5760 | 22800 | 6822 | 16176 | 776 | 8020 | 36 | 14 | 6 | 1 | 90 |

DM = dry matter,
PPM = part per million,
% w/w

The invention claimed is:

1. A process for producing pure lactic acid from a liquid whey by-product that contains at least 30 g/L lactose and at least 1500 ppm chloride, the method comprising the steps of:
   neutralising the whey by-product with a basic metal hydroxide to form a precipitate comprising calcium and phosphate;
   separating the precipitate from the whey by-product to provide a clarified whey by-product;
   incubating the clarified whey by-product with a bacterium capable of bioconversion of lactose to lactic acid to provide a fermentation broth containing lactic acid in the form of a lactic acid salt;
   acidification of the fermentation broth to release lactic acid from the lactic acid salt in order to provide an acidified fermentation broth;
   removing precipitate from the acidified fermentation broth; and
   treatment of the acidified fermentation broth to recover pure lactic acid.

2. A process according to claim 1 in which the basic metal hydroxide is calcium hydroxide or barium hydroxide.

3. A process according to claim 1 in which the whey by-product is selected from whey permeate, concentrated whey permeate, and delactosed whey permeate.

4. A process according to claim 1 in which the whey by-product is concentrated whey permeate having at least 200 g/L lactose or delactosed whey permeate having at least 240 g/L lactose.

5. A process according to claim 1 in which the whey by-product is heated after neutralisation and prior to separation of the precipitate.

6. A process according to claim 1 in which the neutralising and separating steps result in the calcium levels of the whey by-product being reduced by 65% to 85% (dry weight) and the phosphate levels of the whey by-product being reduced by 75% to 95% (dry weight).

7. A process according to claim 1 including a step of filtering the clarified whey by-product using nanofiltration/diafiltration to remove monovalent ions.

8. A process according to claim 1 in which the treatment of the acidified fermentation broth to recover pure lactic acid comprises ultrafiltration to remove proteins, lipids, colour causing particles and high molecular weight compounds.

9. A process according to claim 1 in which the treatment of the acidified fermentation broth to recover pure lactic acid comprises cation exchange and anion exchange steps.

10. A process according to claim 1 in which the whey by-product is the sole source of lactose for the bacteria during the fermentation step.

11. A process according to claim 1 in which the recovered lactic acid has a purity of at least 80% or 90%.

12. A process according to claim 1 in which the recovered lactic acid is L-lactic acid.

13. A process according to claim 1 in which the recovered lactic acid has an isomeric purity of at least 98% L-lactic acid.

14. A process according to claim 1 in which the fermentation broth is treated to remove bacterial cells prior to acidification.

15. A process according to claim 1 in which the fermentation broth is acidified to about pH 2.

16. A process according to claim 1 in which a precipitate formed by acidification is separated from the fermentation broth by centrifugation.

17. A process according to claim 1 in which the acidified fermentation broth is treated with ultrafiltration to provide a lactic acid containing permeate.

18. A process according to claim 1 in which the acidified fermentation broth is treated with ultrafiltration to provide a lactic acid containing permeate, and in which the lactic acid containing permeate is treated with ion exchange to remove ions from the permeate.

19. A process according to claim 18 in which the permeate is treated with cation exchange and anion exchange.

20. The process according to claim 1 in which the bacterium is a *Lactobacillus* strain.

21. The process according to claim 1 in which the bacterium is a *Bacillus* strain.

22. The process according to claim 1 in which the bacterium is a *Bacillus coagulans*.

23. A process according to claim 7 in which the nanofiltration/diafiltration step employs a membrane having a molecular weight cut-off of about 150-300 Daltons and 2 to 5 volumes of diafiltration water.

24. A process according to claim 15 in which the fermentation broth is acidified with sulphuric acid.

25. A process according to claim 17 in which the ultrafiltration employs a membrane having a molecular weight cut-off of between 800 and 1200 Daltons.

* * * * *